(12) United States Patent
Bayly et al.

(10) Patent No.: US 8,419,307 B2
(45) Date of Patent: Apr. 16, 2013

(54) SPREADING IMPLEMENT

(75) Inventors: Peter Bayly, Victoria (AU); Mark Simon Bayly, Victoria (AU); Magnus Ahlstrom, Victoria (AU); Adam Charles Watkinson, Victoria (AU)

(73) Assignee: Acrux DDS Pty Ltd., West Melbourne, Victoria (AU)

( * ) Notice: Subject to any disclaimer, the term of this patent is extended or adjusted under 35 U.S.C. 154(b) by 0 days.

(21) Appl. No.: 13/464,556

(22) Filed: May 4, 2012

(65) Prior Publication Data

US 2012/0220959 A1  Aug. 30, 2012

Related U.S. Application Data

(63) Continuation of application No. 11/678,673, filed on Feb. 26, 2007, now Pat. No. 8,177,449.

(60) Provisional application No. 60/884,482, filed on Jan. 11, 2007.

(51) Int. Cl.
*B43K 1/06* (2006.01)
*A61F 13/00* (2006.01)

(52) U.S. Cl.
USPC ............. 401/265; 401/261; 401/11; 424/443

(58) Field of Classification Search ............... 401/9, 11, 401/261, 264, 265, 266; 424/443
See application file for complete search history.

(56) References Cited

U.S. PATENT DOCUMENTS

| | | | |
|---|---|---|---|
| 1,573,224 A | 3/1924 | Condit | |
| 1,710,816 A | 6/1928 | Evans | |
| 1,925,019 A | 8/1933 | Wilson | |
| 2,361,407 A | 10/1944 | McNair | |
| 2,608,705 A | 8/1946 | Duff | |
| 3,462,230 A | 8/1969 | Chester | |

(Continued)

FOREIGN PATENT DOCUMENTS

| | | |
|---|---|---|
| DE | 28 36 752 | 8/1978 |
| DE | 35 26 109 A1 | 1/1987 |

(Continued)

OTHER PUBLICATIONS

Supplementary European Search Report issued on Mar. 29, 2011 in application No. 07701469.

(Continued)

*Primary Examiner* — David Walczak
(74) *Attorney, Agent, or Firm* — Foley & Lardner LLP

(57) ABSTRACT

Described are methods comprising applying a liquid pharmaceutical testosterone composition with an implement comprising a support and a receptacle mounted on the support and defining a reservoir space with an open top to receive the liquid, wherein the receptacle includes a flexible membrane integrally forming a base and a wall, the wall being substantially transverse to the base and having a working surface to spread the liquid over the treatment surface, wherein the base has a continuous surface such that liquid cannot pass through the base, wherein the wall includes an inner portion which extends from the base to an upper end and an outer skirt portion, wherein the inner portion and skirt portion form a double-wall structure, and wherein at least the wall is resiliently deformable so the working surface maintains contact with the treatment surface when spreading the liquid.

23 Claims, 3 Drawing Sheets

U.S. PATENT DOCUMENTS

| | | | |
|---|---|---|---|
| 3,887,115 | A | 6/1975 | Petterson |
| 4,264,586 | A | 4/1981 | Callingham |
| 4,483,636 | A | 11/1984 | Meyer |
| 4,726,700 | A | 2/1988 | Gray |
| 4,739,778 | A | 4/1988 | Christie |
| 4,787,374 | A | 11/1988 | De Yarman |
| 5,558,874 | A | 9/1996 | Haber et al. |
| 5,568,669 | A | 10/1996 | Godown |
| 5,772,347 | A | 6/1998 | Gueret |
| 5,847,363 | A | 12/1998 | Debourg et al. |
| 5,904,151 | A | 5/1999 | Gueret |
| 6,211,250 | B1 | 4/2001 | Tomlinson et al. |
| 6,299,900 | B1 * | 10/2001 | Reed et al. ............ 424/449 |
| 6,309,128 | B1 | 10/2001 | Griebel et al. |
| 6,315,482 | B1 | 11/2001 | Girardot et al. |
| 6,325,565 | B1 | 12/2001 | Girardot et al. |
| D477,664 | S | 7/2003 | Wong |
| 6,666,216 | B2 | 12/2003 | Bourjal |
| 6,682,757 | B1 | 1/2004 | Wright |
| 6,773,187 | B2 | 8/2004 | Gueret |
| 6,818,226 | B2 | 11/2004 | Reed et al. |
| 6,923,983 | B2 | 8/2005 | Morgan et al. |
| 6,945,723 | B1 | 9/2005 | Gueret |
| 7,927,034 | B2 | 4/2011 | Staniforth et al. |
| 7,955,016 | B2 | 6/2011 | Gueret |
| 2006/0280783 | A1 | 12/2006 | Dipietro et al. |

FOREIGN PATENT DOCUMENTS

| | | |
|---|---|---|
| DE | 197 28 447 | 7/1997 |
| EP | 0 549 049 | 5/1996 |
| FR | 2 581 569 | 11/1986 |
| GB | 1110824 | 4/1968 |
| GB | 1 158 412 | 7/1969 |
| WO | WO 91/18535 | 12/1991 |
| WO | WO 00/06464 | 2/2000 |
| WO | WO 01/76972 A1 | 10/2001 |
| WO | WO 2004/009457 A1 | 1/2004 |
| WO | WO 2005/051771 | 6/2005 |
| WO | WO 2006/005135 A1 | 1/2006 |

OTHER PUBLICATIONS

Notice of Allowance issued on Jan. 23, 2012 by the examiner in U.S. Appl. No. 11/678,673 (US 2008/0170904).

Office Action issued on Oct. 12, 2011 by the Examiner in U.S. Appl. No. 11/678,673 (US 2008/0170904).

Office Action issued on Apr. 4, 2011 by the Examiner in U.S. Appl. No. 11/678,673 (US 2008/0170904).

Office Action issued on Dec. 9, 2010 by the Examiner in U.S. Appl. No. 11/678,673 (US 2008/0170904).

Physicians' Desk Reference, Thomson PDR, 58$^{th}$ ed., pp. 711-713 and 3239-3241, 2004.

Physicians' Desk Reference, Thomson PDR, 60$^{th}$ ed., pp. 722-724 and 3330-3334, 2006.

* cited by examiner

SPREADING IMPLEMENT

This application is a continuation of U.S. patent application Ser. No. 11/678,673, filed Feb. 26, 2007, now U.S. Pat. No. 8,177,449, which claims priority to U.S. Provisional Patent Application No. 60/884,482, filed Jan. 11, 2007.

FIELD

This invention relates to an implement for applying a liquid to a treatment surface. The term liquid as used hereinafter in this specification is intended to be a reference also to liquid like substances such as fluids, lotions, gels, creams or pastes. The implement is particularly suitable for applying a topical or transdermal liquid and it has a particular application in applying a medicated liquid to an area of the body of the user. It will be convenient to hereinafter describe the invention with reference to this particular application, however it is to be appreciated that the implement may be suitable for applying liquids to other treatment surfaces

BACKGROUND

Topical liquids such as sunscreens or medicated liquids have previously been provided in squeezable containers or in containers with a finger operated pump whereby a portion of the liquid is deposited on the treatment surface or on a free hand for subsequent application to the treatment surface. In either case the liquid is spread over the treatment surface with the free hand which results in the liquid being applied to a surface other than the treatment surface. It is not always acceptable for the free hand to be treated with a medicated liquid as the volume dispensed from the container may be a prescribed dose. This is particularly the case where the liquid is intended to have a therapeutic effect at the prescribed dose It is often desirable to provide an implement which temporarily retains the liquid for application to the treatment surface. Implements tend to suffer from the tension between temporarily retaining the liquid and having to release the liquid onto the treatment surface. Implements such as brushes and sponges are effective in spreading the liquid over the treatment surface however they tend to retain a volume of residual liquid after the application of the implement to the treatment surface. The retained volume may vary from application to application and as such it is difficult to accurately apply a metered dose to a treatment surface using an implement such as a brush or sponge. Furthermore the implement can be difficult to clean which can contaminate subsequent liquids particularly if the implement is to be used for a range of medicated liquids.

It would be desirable to provide an implement that was capable of applying a liquid to a treatment surface while minimising retention of residual liquid, and also an implement that was easy to clean after use.

The above discussion of acts, materials, devices, implements and the like is included in this specification solely for the purpose of providing a context for the present invention. It is not suggested or represented that any of these matters formed part of the prior art base or were common general knowledge in the field relevant to the present invention as it existed in Australia before the priority date of this invention.

SUMMARY

According to one aspect of the invention there is provided an implement for applying a volume of liquid to a treatment surface including a support means onto which is mounted, a receptacle defining a reservoir space which receives the volume of liquid, the receptacle having a base and a wall, the wall is substantially transverse to the base and has a working surface that is used to spread the liquid over the treatment surface, at least the wall is resiliently deformable so in use the working surface maintains contact with the treatment surface when spreading the liquid.

It is preferred that the base is resiliently deformable. It is further preferred that the wall is formed integrally with the base from a thin flexible membrane.

It is preferred that the receptacle includes a hinge formation to allow the wall to move relative to the base. It is further preferred that the hinge formation is integrally formed with the base and the wall.

It is preferred that the support means is relatively rigid in comparison to the at least the wall of the receptacle so that at least the wall is movable relative to the support means when applying the liquid. It is further preferred that the support means is releasebly attached to the receptacle. It is further preferred that the wall includes a skirt portion a lower edge of which is attached to the support means. It is also preferred that the support means is detachably connectable to a dispensing means that is operable to dispense the volume of liquid into the receptacle.

It is preferred that the wall includes an inner portion that is located between the skirt and the base. It is further preferred that the inner portion extends from the base at an angle greater than or equal to 90° and is continuous from the base to the working surface.

It is preferred that at least the inner portion includes a plurality of channels providing a passageway for the liquid from the reservoir space to the treatment surface. It is further preferred that the wall is castellated between the inner portion and the skirt with an exit end of each channel spacing each castellation. It is further preferred that the working surface is limited to the castellation.

It is preferred that the working surface extends along the wall between the inner portion and the skirt. The working surface may cover the inner portion of the wall and may also cover the skirt of the wall. It is further preferred that the working surface is substantially convex.

It is preferred that the skirt flares outwardly from the support means towards the working surface. Alternatively the skirt is substantially parallel to the inner portion.

It is preferred that the treatment surface is the user's skin. It is further preferred that the treatment surface is the axilla area of the users skin.

It will be convenient to hereinafter describe the invention in greater detail by reference to the accompanying drawings showing four example embodiments of the invention. The particularity of the drawings and the related detailed description is not to be understood as superseding the generality of the preceding broad description of the invention.

DETAILED DESCRIPTION

Figure 1:
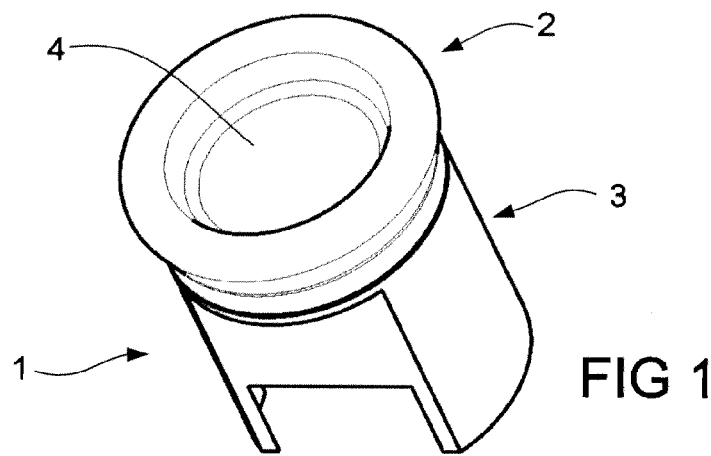
FIG. 1 is an isometric view of an implement according to a first preferred embodiment of the invention.

Referring firstly to FIG. 1 which shows a first preferred embodiment of the implement 1 which includes a receptacle 2 and a support means 3 for supporting the receptacle 2. The receptacle 2 defines a reservoir space 4 for receiving a volume of liquid. When the implement 1 is in use the receptacle 2 is brought into engagement with a treatment surface (not shown) so as to enable the liquid to be transferred and spread over a treatment surface by a working surface of the receptacle 2. The treatment surface may be any surface however the implement has been designed with the intention being that the treatment surface is the user's skin and in particular the axilla area of the users skin.

Figure 2:
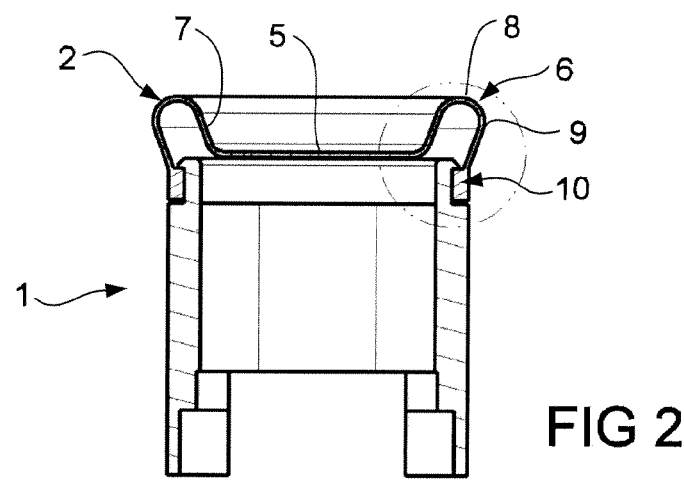
FIG. 2 is a cross sectional view of the implement from FIG. 1.
Figure 3:
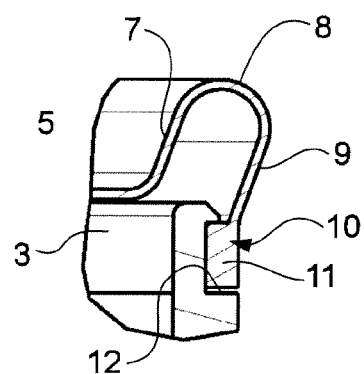
FIG. 3 is a detailed view of part of the implement from area A of FIG. 2.

Referring now to FIG. 2 which shows the implement 1 in cross section and it can be noted that the receptacle 2 includes a base 5 and a wall 6. The wall includes an inner portion 7 which extends continuously from the base 5 towards an upper end 8 of the wall 6. A skirt portion 9 of the wall extends continuously from the upper end 8 of the wall to a lower edge 10 which is attached to the support means 3. FIG. 3 shows more clearly the lower edge of the skirt being formed with a thickened rib 10 which locates in a recess 12 formed on the support means 3. Other means for connecting the receptacle to the support means are clearly possible however this arrangement allows the receptacle 2 to be detached from the support means 3 for purposes such as cleaning of the receptacle 2.

It is preferred that at least the top end 8 of the wall 6 is resiliently deformable in use when contacting the treatment surface. The portion of the wall 6 that engages the treatment surface provides the working surface which is used to spread the liquid over the skin. Accordingly the working surface may include the inner portion 7, the upper end 8 and/or the skirt portion 9. In the preferred embodiment illustrated in FIGS. 2 and 3 the receptacle 2 is formed from a relatively flexible membrane which allows at least the wall 6 to flex acting as a blade-like member when spreading the liquid across the treatment surface. The relative flexibility of the membrane allows the wall 6 to roll across the treatment surface spreading the liquid rather than wiping the liquid off the treatment surface.

Figure 4:
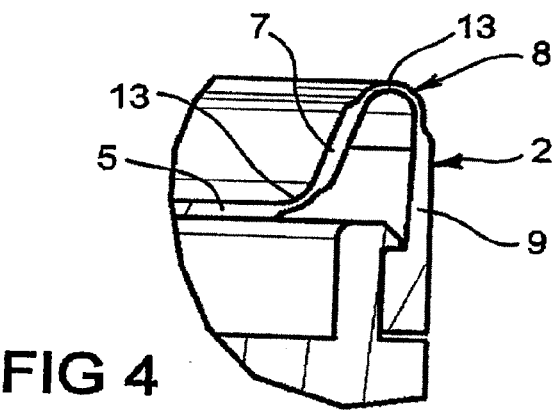
FIG. 4 is a detailed view of part of the implement in cross section according to a second preferred embodiment of the invention.

In a second preferred embodiment as illustrated in FIG. 4 the receptacle 2 is formed with two hinge formations 13. The hinge formation 13 is achieved by a localised reduction of the thickness of the membrane. This allows for example for the inner portion 7 of the wall to more easily flex relative to the base 5 of the receptacle. The hinge formation 13 at the upper end 8 of the wall allows the inner portion 7 of the wall to flex relatively to the skirt portion 9. This effectively creates a finer edge for the blade-like member.

Figure 5:
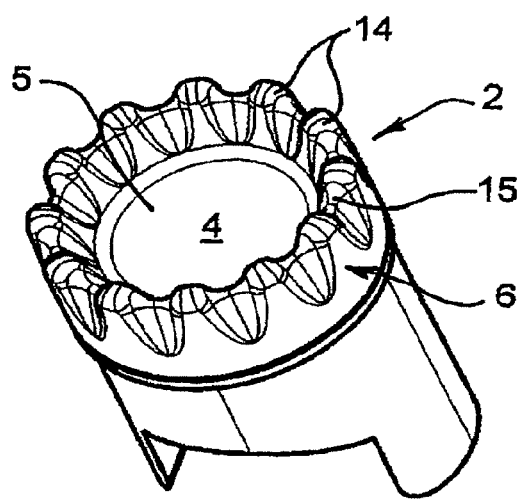
FIG. 5 is an isometric view of an implement according to a third preferred embodiment of the invention.
Figure 6:
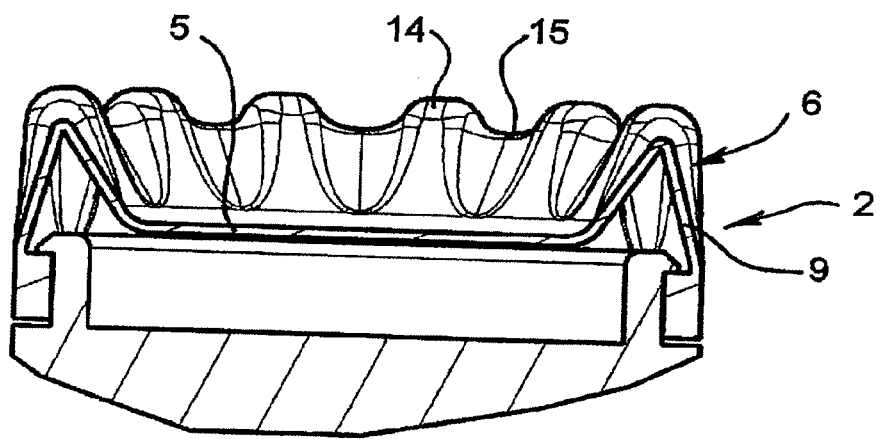
FIG. 6 is a cross sectional view of part of the implement from FIG. 5.

Referring now to a third preferred embodiment of the receptacle 2 as illustrated in FIGS. 5 and 6 which show the wall 6 being formed with castellations 14 at the upper end thereof. The castellations 14 are each spaced by a channel 15 which extends substantially from the base 5 towards the upper end of the wall 6. Each channel 15 provides a passage way for the liquid to egress from the reservoir space 4 towards the working surface. The castellation 14 at the upper end of the wall 6 reduces the surface area of the working surface which allows the liquid to be transferred to the treatment surface in a thicker layer. The channels 15 are illustrated as extending to the skirt 9 however this is not essential so long as the channels 15 extend from the reservoir space 4 to the working surface of the wall, and that the castellations occupy the working surface.

Figure 7:
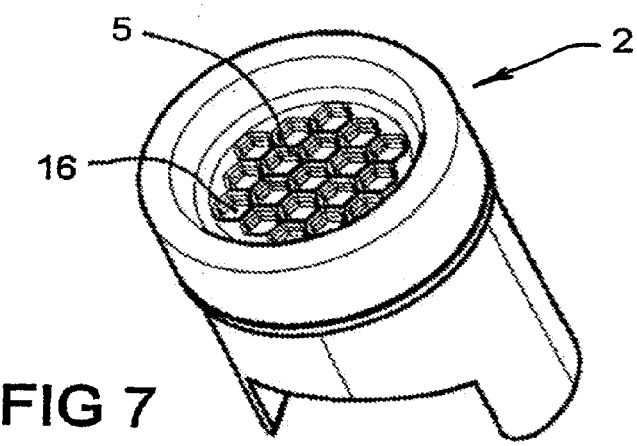
FIG. 7 is an isometric view of an implement according to a fourth preferred embodiment of the invention.

Referring now to FIG. 7 which shows the fourth preferred embodiment of the receptacle 2. In this preferred embodiment the base 5 of the receptacle 2 is formed with a plurality of dimples 16. The illustration shows each dimple 16 being in the form of a hexagon however this is not essential. The provision of the dimples 16 makes the receptacle 2 easier to fill in that the liquid is less likely to bounce out of the reservoir space 4.

Figure 8:
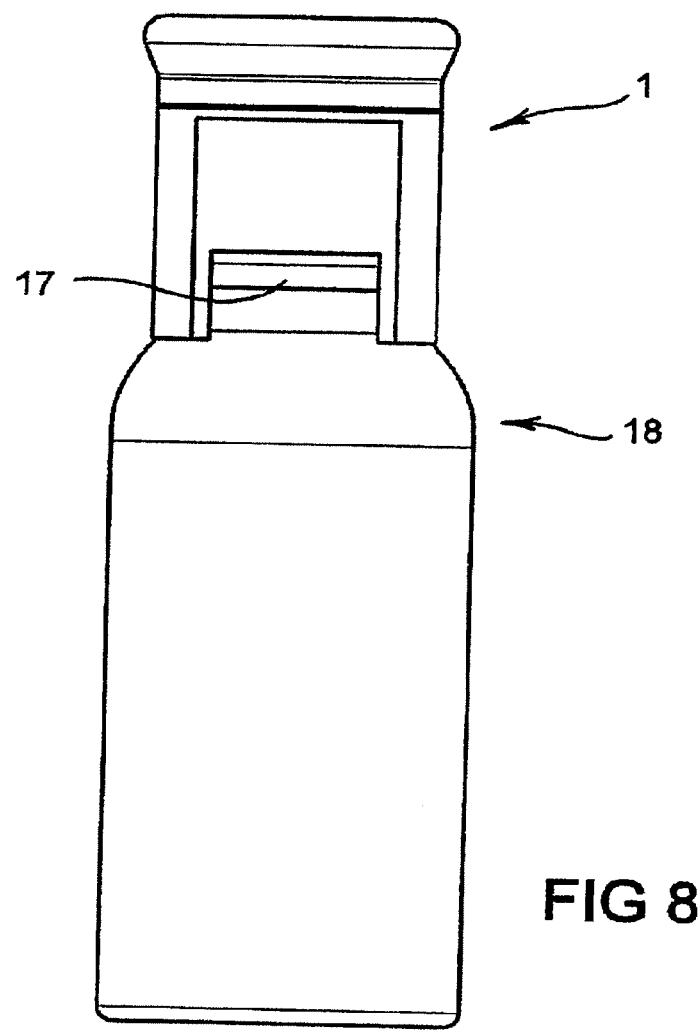
FIG. 8 is a front elevation view of the implement from FIG. 1 connected to a dispensing means.

Referring now to FIG. 8, it is preferred that the implement 1 be detachably connectable to a dispensing means 17 or some other portion of a container 18 that contains a bulk volume of the liquid. Where the dispensing means 17 is in the form of a pump 17 the implement 1 may engage the pump 17 in such a way as to reduce the exposure of the outlet of the pump to air. This will reduce the likelihood that the pump suffers from issues such as loss of prime. Furthermore the relatively solid nature of the support means 3 surrounding the pump 17 will reduce the likelihood of inadvertent discharge from the pump 17.

It will be apparent from the foregoing description that an implement 1 incorporating the invention provides an effective and easy to use means for applying and spreading liquid over a treatment surface. The implement 1 is less likely to retain residual liquid than say a sponge or brush. The castellations 14 with channel 15 formations provides a unique advantage in that the implement can spread a thicker layer of liquid over the treatment surface.

In one particularly preferred embodiment of the invention the liquid contained in the container is a transdermal drug delivery composition, particularly a transdermal drug delivery composition of the type described in U.S. Pat. No. 6,299,900 or WO 2006/128255 the contents of each of which are herein incorporated by reference. The liquid may and preferably will be in the form of a gel, cream, foam or viscous solution when delivered to the receptacle.

According to a further aspect of the invention thus provides a system for transdermal administration of a physiologically active agent from a liquid composition, the system including a container containing the liquid composition including the physiologically active agent, a dispensing means for delivering liquid from the container; and an applicator for applying the liquid to an area of skin for transdermal administration said applicator including a receptacle defining a reservoir space which receives a volume of liquid from the container, the receptacle having a base and a wall substantially transverse to the base having a working surface that is used to spread the liquid over the area of the skin surface wherein at least the wall is resiliently deformable so in use the working surface maintains contact with the treatment surface when spreading the liquid.

The applicator may be removably mountable on the container or container lid to allow convenient application of liquid to the receptacle and cleaning or replacement.

The liquid will preferably comprise a volatile liquid, a physiologically active agent and preferably a viscosity modifying agent.

The volatile liquid (also sometimes called a "volatile carrier" or "vehicle") will typically be present in a higher concentration, such as 80% or more w/w. The volatile liquid may be any solvent that is pharmacologically suitable and many such solvents are known in the art. One of the advantages of the inclusion of a volatile solvent or volatile carrier is that it facilitates the composition to dry rapidly, allow the absorption of the active agent, and avoid the problems of accidentally dosing others by confining administration to a small area of skin, preferably the axilla. Preferably the volatile liquid is a solvent having a vapour pressure above 35 mm Hg at atmospheric pressure and normal skin temperature of 32 degrees Celsius. Preferably, the solvent is a lower alkyl alcohol or a mixture of such alcohols. Suitable solvents include ethanol, ethyl acetate, isopropanol, acetone, ethyl formate, methyl acetate, methyl ethyl ketone, pentane and chloroform or mixture thereof in the range of about 40 to 99% v/v of the composition, preferably more than 50%, 60%, 70% or 80%. An aerosol propellant, such as dimethyl ether or R134a, may also constitute a volatile liquid for the purpose of the present invention.

The composition may include a viscosity modulating agent. The term "viscosity modulating agent" is used to refer to a component of the composition which alters the viscosity of the overall resulting composition. The nature of the viscosity modulating agent depends not only on the agent itself, but also the proportion in which it is present and the presence or absence of other components. For example, a gelling agent may act as a viscosity modulating agent providing that an activator for that gelling agent is present. For example, hydroxypropylmethylcellulose (HPMC) may be used in a composition with an activator, in which the volatile solvent is a lower alkyl alcohol at a concentration of around 2% w/w. A suitable activator would be sodium chloride. Concentration may be important as, in this example, at 0.1% w/w HPMC has different effects. A thickening agent is one which increases viscosity, and is often anhydrous.

The viscosity modulating agent will commonly be a thickening agent or a gelling agent. It will often be used to increase the viscosity of the composition containing a solution of the physiologically active agent in the volatile solvent. Given the nature of the volatile solvents, the solution will typically have very low viscosity. The purpose of the viscosity modulating agent is to increase the viscosity of the solution such that the composition is retained in the vicinity of the area of application for a brief period of time so as to permit increased uptake of the physiologically active agent at that site. The viscosity modulating agent preferably increases the viscosity to about that of a typical lotion (eg, sunscreen), but not to the point where the composition becomes a gel. Typically, the viscosity of a transdermal drug delivery composition according to the invention will be less than 300 centipoise and often about 150 centipoise.

The viscosity modulating agent must retain its activity in the context of the other components of the composition of the invention. In particular, the thickening agent must remain active and stable in this environment. For example, where the composition has a high alcohol content (for example, where the volatile solvent comprises primarily alcohol at greater than 80% v/v), the thickening agent must be effective in a high alcoholic environment. Having these requirements in mind, a skilled person can select several thickening agents from those known in the art. Desirably, a thickening agent also inhibits the solvent evaporation rate from the composition so as to enhance the so-called "solvent burst" of active agent into the skin at the site of application. In one embodiment the thickening agent includes polyvinyl pyrrolidone or PVP (Povidone™).

It will be appreciated by one skilled in the art that the amount of thickening agent required is a question of degree and compromise with other parameters. It is also known that many thickening agents have peak activity at a particular concentration, and that activity may drop off substantially with slightly higher and slightly lower percentage concentrations. For example, in one preferred embodiment where the composition comprises over 80% alcohol and the thickening agent used is PVP, the desirable concentration of PVP is between 1 and 3%, and its activity is substantially reduced outside that range.

Gelling agents are matrix-forming agents which, once activated, act by forming a matrix within and around the composition they are in. Thickening agents are usually anhydrous agents which increase the viscosity of the composition.

The physiologically active agent may be selected from any of the agents described in U.S. Pat. No. 6,299,900 and WO2006/128255, the contents of each of which are herein incorporated by reference. Physiologically active agents that may be used in the system of the present invention include any locally or systemically active agents which can be delivered through the skin to achieve a desired effect. These active agents (grouped by therapeutic class) may include:

(a) Alimentary System agents including antidiarrhoeals.
(b) Cardiovascular System agents including:
  (i) antihypertensives;
  (ii) calcium channel blockers;
  (iii) antiarrhyrthmics;
  (iv) antiangina agents;
  (v) beta-adrenergic blocking agents;
  (vi) cardiotonic glycosides;
  (vii) adrenergic stimulants;
  (viii) vasodilators; and
  (ix) antimigraine preparations.
(c) Drugs Affecting Blood and Haemopoietic Tissues including:
  (i) anticoagulants and thrombolytic agents; and
  (ii) haemostatic agents.
(d) Drugs Affecting the Central Nervous System including:
  (i) analgesics;
  (ii) antipyretics; and
  (iii) others including acetylsalicylic acid (aspirin), paracetamol, and phenazone.
(e) Hypnotics and sedatives.
(f) Antianxiety agents.
(g) Neuroleptic and antipsychotic drugs.
(h) Antidepressants, tetracyclic antidepressants, monoamine oxidase inhibitors and selective serotonin re-uptake inhibitors.
(i) CNS stimulants.
(j) Anti-alzheimer's agents.
(k) Antiparkinson agents and dopamine-2 agonists.
(l) Anticonvulsants.
(m) Antiemetics, antinauseants and 5HT-3 receptor antagonists.
(n) Musculoskeletal System including:
  (i) Non-steroidal anti-inflammatory agents;
  (ii) Additional non-steroidal antiinflammatory agents;
  (iii) Antirheumatoid agents;
  (iv) Muscle relaxants; and
  (v) Agents used in gout and hyperuricaemia.
(o) Hormones and Steroids including:
  (i) oestrogens and derivatives thereof;
  (ii) progesterone and other progestagens and derivatives thereof;
  (iii) antiandrogens;
  (iv) antioestrogens and derivatives.
  (v) androgens and anabolic agents and derivatives thereof;
  (vi) 5-alpha reductase inhibitors;
  (vii) corticosteroids;

(viii) further steroidal antiinflammatory agents;
(ix) pituitary hormones and their active derivatives or analogs;
(x) thyroid hormones; and
(xi) other miscellaneous hormone agents such as octreotide.
(q) Pituitary inhibitors.
(r) Ovulation inducers.
(s) Hypoglycaemic agents.
(t) Genitourinary System agents.
(u) Diuretics. related diuretics and loop diuretics.
(v) Antidiuretics including their active derivatives or analogs.
(w) Obstetric drugs including agents acting on the uterus.
(x) Prostaglandins.
(y) Antimicrobials including:
   (i) cephalosporins;
   (ii) penicillins;
   (iii) tetracyclines and other tetracycline-type antibiotics;
   (iv) minoglycosides;
   (v) quinolones.
   (vi) sulphonamides;
   (vii) sulphones; and
   (viii) other miscellaneous antibiotics.
(z) Antituberculosis drugs.
(aa) Antimalarials.
(ab) Antiviral agents.
(ac) Anthelmintics.
(ad) Cytotoxic agents.
(ae) Metabolism agents including anorectic and weight reducing agents.
(af) Agents used in hypercalcaemia and their active derivatives or analogs.
(ag) Respiratory System agents including:
   (i) antitussives;
   (ii) expectorants;
   (iii) decongestants; and
   (iv) bronchospasm relaxants and prodrugs and derivatives thereof.
(ah) Allergy and Immune System agents including:
   (i) antihistamines.
(ai) Local anaesthetics.
(aj) Stratum corneum lipids.
(ak) Neuromuscular blocking agents.
(al) Smoking cessation agents.
(am) Insecticides and other pesticides which are suitable for local or systemic application.
(an) Dermatological agents.
(ao) Allergens for desensitisation.
(ap) Nutritional agents.
(aq) Keratolytics.
(ar) Psychicenergisers.
(as) Anti-acne agents.
(at) Anti-psoriasis agents.
(au) Anti-itch agents.
(av) Anticholinergic agents.
(aw) Other physiologically active peptides and proteins including small to medium-sized peptides.

It is particularly preferred that the active is effective via the systemic circulation and still more preferably the active agent comprises a hormone, particularly selected from the group consisting of oestrogens, progestins and androgens, including prodrugs and derivatives thereof. Most preferably the active agent comprises testosterone or a derivative or prodrug thereof.

The preferred active agent is testosterone or a derivative thereof, which may be used in the treatment of testosterone deficiency in men and women and the conditions and diseases resulting therefrom. The composition may therefore comprise testosterone or a derivative thereof. There are number of closely related androgenic compounds which are synthetically derivatized from testosterone are known to provide the same or a similar physiologic activity. Such compounds include without limitation, testosterone salts, such as acetate, enanthate, cypionate, isobutyrate, propionate, undecanoate esters, cyproterone acetate, danazol, finasteride, fluoxymesterone, methyltestosterone, nandrolone decanoate, nandrolone phenpropionate, oxandrolone, oxymetholone, stanozolol, and testolactone. Contrary to what might be expected from the activity of testosterone, the applicant has found that the invention may be used to provide rapid delivery of testosterone for transdermal administration of without inducing unacceptable levels of side effects that distress a subject such as sweating and odor, which have been attributed to the presence of elevated testosterone.

Testosterone production in both men and women declines naturally with age. Testosterone deficiency may result from disease or damage to the hypothalamus, pituitary gland, or testicles that inhibits hormone secretion and testosterone production, and is also known as hypogonadism. Depending on age, insufficient testosterone production can lead to abnormalities in muscle and bone development, underdeveloped genitalia, and diminished virility.

Testosterone deficiency in men (hypogonadism) may be present at birth (congenital) or may develop later (acquired). It is classified by the location of its cause along the hypothalamic-pituitary-gonadal axis:
Primary, disruption in the testicles
Secondary, disruption in the pituitary
Tertiary, disruption in the hypothalamus.

The most common congenital cause is Klinefelter's syndrome. This condition, which is caused by an extra X chromosome, results in infertility, sparse facial and body hair, abnormal breast enlargement (gynecomastia), and small testes.

Congenital hormonal disorders such as leutenizing hormone-releasing hormone (LHRH) deficiency and gonadotropin-releasing hormone (GnRH) deficiency (e.g., Kallmann's syndrome) also may cause testosterone deficiency.

Other congenital causes include absence of the testes (anorchism; also may be acquired) and failure of the testicles to descend into the scrotum (cryptorchidism).

Acquired causes of testosterone deficiency include chemotherapy; damage occurring during surgery involving the pituitary gland, hypothalamus, or testes; glandular malformation; head trauma that affects the hypothalamus; infection (e.g., meningitis, syphilis, mumps); isolated LH deficiency (e.g., fertile eunuch syndrome); radiation; testicular trauma; and tumors of the pituitary gland, hypothalamus, or testicles.

Androgen deficiency in women has been associated with an increased rate of sexual problems or complaints in a number of studies. These problems are frequently encountered in oophorectomized women and those with androgen deficiency from other causes. Hypoactive sexual desire disorder (HSDD) in women is the persistent or recurring deficiency (or absence) of sexual fantasies, thoughts and/or desire for, or receptivity to, sexual activity, which causes personal distress. The cause may be either physiological or psychological or a combination of both. Common physiological etiologies include hormone deficiencies, medications, and surgical interventions. Any disruption of the female hormonal milieu caused by these etiologies can result in decreased sexual desire. The lack of, or a decrease in, sexual desire may also be secondary to poor sexual arousal and response, or to pain associated with sexual activity. Another factor may be difficulty with inability to attain or maintain sufficient sexual excitement, a condition known as female sexual arousal disorder (FSAD).

The invention may be used in the treatment of sexual dysfunction in men and women.

Normal daily production of testosterone in normal young men ranges from 3-10 mg per day with diurnal variation (maximum ~7 am declining throughout the day). The aim of testosterone therapy in men is to deliver physiologic amounts of testosterone to the systemic circulation producing serum testosterone levels within the normal range for healthy men (e.g. 300-1000 ng/dL or 10-35 nM).

Several clinical studies have demonstrated that in conditions such as female sexual dysfunction, testosterone administration, which is aimed at restoring testosterone levels to normal reproductive levels, is effective in improving sexual function. The studies to date suggest that systemic administration of doses ranging from 150 μg to 300 μg a day would be sufficient to return testosterone levels to mid- to high premenopausal levels in androgen deficient women.

In one embodiment, the invention is used to deliver a composition containing testosterone as the active agent to the axilla of a patient to result in a blood level of testosterone of at least a predetermined amount. In one embodiment, the predetermined amount is the normal range. In the case of testosterone, the blood level achieved is at least 200 ng/dL, preferably 300-1000 ng/dL.

The invention may be used in the treatment of a wide variety of conditions responsive to testosterone therapy such as AIDS Wasting Syndrome, micropenis, somatopause, andropause, viropause, or androgen deficiency in adult males (ADAM), anemia from renal dialysis or chronic kidney disease, benign prostatic hyperplasia, acne, diabetes, infertility, periodontal disease, post anabolic steroid abuse, dry eyes, diabetic retinopathy, retinopathy, and Lupus Erythematosis decreased bone density (i.e. osteoporosis), hyperlipemia, predisposition toward prostrate cancer, heart disease, angina, and hypertension.

In further embodiments, the invention may be used in a method of treatment of oestrogen and/or progestin deficiency, a method of treatment of chronic pain, and a method of treatment of anxiety related disorders.

The composition may have antiperspirant and/or deodorant properties. The composition therefore allows the active agent to be rapidly delivered for transdermal administration whilst also enabling perspiration and/or odor to be reduced. The invention facilitates delivery of the composition to areas such as the axilla for transdermal drug delivery without patient inconvenience of not using normal antiperspirant/deodorant products (important for patient compliance) which may otherwise interfere with delivery of the active.

The antiperspirant and/or deodorant properties of the composition are particularly advantageous when the physiologically active agent is testosterone or derivatives thereof for treating testosterone deficiency in a subject. Testosterone is responsible for increasing perspiration and producing perspiration and perspiration related odor in the presence of 5-alpha-reductase, due to the conversion of testosterone to dihydrotestosterone (DHT).

In one embodiment, the thickening agent may be an antiperspirant and/or an occlusive agent for the drug delivery composition. In another embodiment, both a deodorant and an antiperspirant are in a composition with the at least one active agent and a dermal penetration enhancer. Suitable thickening agents include polyvinyl pyrrolidone or PVP (Povidone™). The antiperspirant may be an occlusive agent also, and a thickening, occlusive agent may have antiperspirant effects.

In some embodiments, the thickening agent is an antiperspirant or the composition further includes an antiperspirant and/or a deodorant.

Despite the inherent antiperspirant and/or deodorant properties of the composition, the composition may be optionally administered with deodorant and antiperspirant additives that do not interfere with the active. In another form, the liquid may comprise at least one physiologically active agent; and at least one volatile solvent; and at least one antiperspirant or deodorant.

In one embodiment, the composition comprises an antiperspirant agent. The antiperspirant agent may be any suitable substance that reduces or inhibits the production of sweat. In some instances, an antiperspirant agent can also provide deodorancy benefits.

Preferably, the antiperspirant agent is selected from the group consisting of inorganic or organic salts of aluminium, zirconium, zinc or mixtures thereof.

In one embodiment, the antiperspirant agent is an aluminium salt having the general formula:

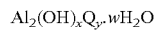

where Q is chlorine, bromine or iodine;
x is 2 to 5;
x+y=6, where x and y do not need to be integers; and
wH$_2$O represents a variable amount of hydration.

In another embodiment, the antiperspirant agent is a zirconium salt of the following general formula:

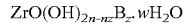

where
z is a variable in the range of from 0.9 to 2.0 so that the value of 2n−nz is zero or a positive;
n is the valency of B;
B is selected from the group consisting of chloride, other halide, sulphamate, sulphate and mixtures thereof; and
wH$_2$O represents a variable amount of hydration.

In a preferred embodiment, the antiperspirant agent is selected from the group consisting of aluminium chloride, aluminium chlorohydrate, aluminium chlorohydrex polyethylene glycol, aluminium chlorohydrex propylene glycol, aluminium dichlorohydrate, aluminium dichlorohydrex polyethylene glycol, aluminium dichlorohydrex propylene glycol, aluminium sesquichlorohydrate, aluminium sesquichlorohydrex polyethylene glycol, aluminium sesquichlorohydrex propylene glycol, aluminium zirconium octachlorohydrate, aluminium zirconium octachlorohydrex gly, aluminium zirconium pentachlorohydrate, aluminium zirconium pentachlorohydrex gly, aluminium zirconium tetrachlorohydrate, aluminium zirconium tetrahlorohydrex gly, aluminium zirconium trichlorohydrate and aluminium zirconium trichlorohydrex gly. These antiperspirant agents have approved listings under the United States Food & Drug Administration Federal Register.

It is contemplated that other antiperspirant agents may also be used. Examples of these antiperspirant agents include aluminium bromohydrate, aluminium chloride, aluminium citrate, aluminium sulfate, ammonium alum, cobalt acetylmethionate, potassium alum, sodium alum and sodium aluminium chlorohydroxy lactate.

In another embodiment, the composition comprises a deodorant agent. The deodorant agent may be any suitable substance that provides deodorancy benefits in masking or neutralising odors that are produced by the action of bacteria.

Generally, deodorant agents do not interfere with the production of perspiration. Representative examples of deodorant agents include, but are not limited to, one or more of cetyltrimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmithyl sarcosine, lauroyl satcosine, N-myristoyl glycine, potassium N-lauryl sarcosine, stearyl, trimethyl ammonium chloride, sodium aluminium chlorohydroxy lactate, tricetyl methyl ammonium chloride, 2,4,4'-trichloro-2'-hydroxy diphenyl ether, diaminoalkyl amides such as L-lysine hexadecyl amide, heavy metal salts of citrate, salicylate, and piroctose, especially zinc salts, and acids thereof, heavy metal salts of pyrithione, especially zinc pyrithione and zinc phenolsulfate. Other deodorant agents include, without limitation, odor absorbing materials such as carbonate and bicarbonate salts, e.g. as the alkali metal carbonates and bicarbonates, ammonium and tetraalkylammonium carbonates and bicarbonates, especially the sodium and potassium salts, or any combination of the above In a preferred embodiment, the composition comprises a combination of antiperspirant and deodorant agents. The antiperspirant and deodorant agents may be present in the composition in any amount that provides beneficial antiperspirant and/or deodorancy effects. The antiperspirant agent or deodorant agent may be present in an amount of from about 0.05 to 60%, and is preferably from about 1 to 40%, more preferably from about 5 to 30% and even more preferably from about 8 to 15% by weight of the composition. Where the composition comprises a combination of antiperspirant and deodorant agents, the combined amounts of these agents is preferably within the preferred range stated above.

In one embodiment, the composition may comprise a penetration enhancer. The penetration enhancer is also sometimes called an "absorption" enhancer. Suitable dermal penetration enhancers are described in U.S. Pat. No. 6,299,900 and WO 2006/128255, the contents of each of which are herein incorporated by reference. The preferred dermal penetration enhancers include: fatty acids, fatty acid esters, fatty alcohols, glycols and glycol esters, 1,3-dioxolanes and 1,3-dioxanes, macrocyclic ketones containing at least 12 carbon atoms, oxazolidinones and oxazolidinone derivatives, alkyl-2-(N,N-disubstituted amino)-alkanoate esters, (N,N-disubstituted amino)-alkanol alkanoates, sunscreen esters and mixtures thereof. These include the compounds being safe skin-tolerant ester sunscreens of formula:

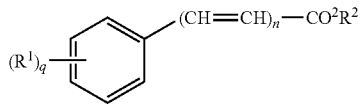

(I)

wherein $R^1$ is hydrogen, lower alkyl, lower alkoxy, halide, hydroxy or $NR^3R^4$;
$R^2$ is long chain alkyl;
$R^3$ and $R^4$ are each independently hydrogen, lower alkyl or $R^3$ and $R^4$ together with the nitrogen atom to which they are attached form a 5- or 6-membered heterocyclic ring;
n is 0 or 1; and
q is 1 or 2.

Most preferably the dermal penetration enhancer is selected from the list including oleic acid, oleyl alcohol, cyclopentadecanone (CPE-218™), sorbitan monooleate, glycerol monooleate, propylene glycol monolaurate, polyethylene glycol monolaurate, 2-n-nonyl 1,3-dioxolane (SEPA™), dodecyl 2-(N,N-dimethylamino)-propionate (DDAIP) or its salt derivatives, 2-ethylhexyl 2-ethylhexanoate, isopropyl myristate, dimethyl isosorbide, 4-decyloxazolidinon-2-one (SR-38™,TCPI, Inc.), 3-methyl-4-decyloxazolidinon-2-one, octyl dimethyl-para-aminobenzoate, octyl para-methoxycinnamate, octyl salicylate and mixtures thereof.

The concentration of absorption/penetration enhancer may be in the range from 10-10,000 weight percent of absorption/penetration enhancer based upon the weight of active ingredient. The ratio of penetration enhancer to active ingredient may vary considerably and will be governed as much as anything, by the pharmacological results that are required to be achieved. In principle, it is desirable that as little absorption enhancer as possible is used. However, it is most preferable that the penetration enhancer be in the range from 0.01-15% of the total composition.

In the most preferred embodiment of the invention the composition is formulated to dry on the skin within three minutes of application. In this way the composition is driven into the skin to form a reservoir of the physiologically active agent in the skin which we have found is particularly active in enhancing blood levels without the undesirable effects associated with high localised subcutaneous levels in the region of application. Pharmacodynamically, delivery of the active is substantially "steady-state", once a reservoir of the active is established in the skin.

The composition preferably has a drying time of less than three minutes. Drying time may be determined by in vitro or in vivo tests. A suitable in vitro test involves placing a 10 µL_sample on a clean glass slide at room temperature (approx 20° C.) and using a four decimal place analytical balance the time take for the vehicle to stop evaporating is measured. The resulting drying times from three repetitions of the test may be averaged.

For in vivo drying time measurement 10 µLs applied to volar forearms (32° C.) of three subjects and the drying time is measured by touch and visual verification (no visible surface vehicle or shine).

Preferably the composition is non-occlusive, in that in the broadest sense, the composition is not trapped to the skin, or the skin is not closed to the atmosphere, by means of a patch device, fixed reservoir, application chamber, tape, bandage, sticking plaster, or the like, which remains on the skin a the site of application for a prolonged length of term. Such devices tend to be uncomfortable for the wearer or can be embarrassing or unsightly.

In one embodiment, the composition appears like a lotion. In this context, "lotion" is used in its broad descriptive sense, rather than the more specific formulatory sense which refers to a mixed phase or suspension of active. The composition is often a true solution, but with increased viscosity so that its viscosity is more similar to that usually associated with a lotion. The viscosity of the composition is preferably greater than that of water but less than about 300 centipoise. The viscosity in different embodiments is in the range of 10 to 200, 20 to 100 or 30 to 50 centipoise.

Without being bound by any theory, the applicant believes that the viscosity modulating agent and/or penetration enhancer in the composition function to minimise perspiration, and that the volatile carrier functions to inhibit bacteria and therefore odor by a bactericidal activity of the carrier.

In one embodiment, the composition consists essentially of one physiologically active agent; one volatile solvent; and one viscosity modulating agent, each as described above. Preferably, it further includes a penetration enhancer as described above. In one embodiment, the viscosity modulating agent is an antiperspirant, and the composition optionally also includes a deodorant. Each of these embodiments may or may not also include water.

In another embodiment, the composition may include at least one additional active agent and/or at least one additional inactive agent. In a different embodiment, the composition does not include a herbal extract (or like component), whether as a physiologically active agent or otherwise.

The composition may be applied to the skin, including but not limited to axilla, of a subject in any of a range of forms. Suitable forms include for example lotions, creams, gels, foams, pastes, solutions, sprays, aerosols, roll-ons and the like. The composition may be applied in an occlusive or non-occlusive manner. It is preferred that the composition is applied in a non-occlusive manner and in the most preferred embodiment the composition is formulated for application as a lotion, gel, cream, foam or viscous solution. Generally, the properties of the composition are such that it can be readily dispensed and spread by the implement of the invention. The composition can be formulated by adding suitable carriers, excipients and thixotropic agents which are inert to the active to facilitate dispensing and spreading of the composition and thus delivery of the composition to the skin for transdermal administration of the active agent.

The composition may further comprise additional components that will facilitate its preparation into forms suitable for application to the axilla of a subject. Examples of additional components include but are not limited to surfactants, buffers, solvents and propellants.

In one embodiment, the composition comprises a volatile carrier which is isopropyl alcohol, a penetration enhancer which is octisalate, an active agent which is testosterone and a thickening agent which is polyvinylpyrrolidone. These may be in the following percentages:

30% v/v carrier;
8% w/v enhancer;
1% w/v active;
2% w/v thickener;
10% v/v sterile water; and
the balance ethanol.

In one embodiment, the invention utilises a transdermal drug delivery composition consisting essentially of the above 6 components in those proportions.

Other actives as set-out below are also contemplated for use in the composition.

In another embodiment, the composition may further include a second active agent to provide the composition with additional usage benefits. The second active agent may be selected from any one of the active agents listed above, or herbal extracts and/or cosmetic agents (such as, age spot and keratose removing agents, anti-aging agents, antioxidants, and hydroxy acids).

Preferably the second active agent is an antifungal agent. Fungal infections are common in areas of the body having higher production of heat and perspiration.

In yet another embodiment, the composition may further comprise one or more inactive agents. Such inactive ingredients may be referred to as "additives". Examples of such additives include but are not limited to, humectants, deodorant agents, antiperspirants, pH adjusting agents, preservatives, emulsifiers, occlusive agents (including without limitation patches and film formers), solubilizing agents, colorants, and surfactants (including without limitation anionic surfactants).

In yet another embodiment the invention provides a method of transdermal administration of a physiologically active agent to a subject including
providing an implement as hereinbefore described;
applying a liquid including the physiologically active agent to the reservoir; and
deforming the wall of the receptacle containing the liquid against the skin of the subject and spreading the liquid over the area of the skin surface preferably in at least one axilla. The receptacle is preferably used so as to maintain the working surface in contact with the treatment surface when spreading the liquid.

The method can be used to deliver a predetermined amount of active and/or sufficient active to achieve a predetermined bloodstream level or concentration of the active. For some actives (eg, those with a short half-life) other measures of the amount of active delivered will be appropriate.

In another embodiment the invention provides use of a physiologically active agent in manufacture of a medicament for treatment of a subject by application to the skin of the subject in at least one axilla with the above described implement. The medicament is preferably for treatment or prevention of a condition treatable or preventable by the active.

The invention is described with reference to the following Example. It is to be understood that the Example is provided by way of illustration of the invention and is not limiting to the scope of the invention.

EXAMPLE

The above described implement, such as the implement of FIGS. 5 and 6 may be used to apply the composition of Example 1 of WO 2006/128255 to at least one axilla of a male or female human to treat conditions arising from deficient systemic testosterone blood levels:

The composition of Example 1 of WO 2006/128255 contained the following components in the amounts by weight specified.

| Component | Use | Concentration |
|---|---|---|
| Octisalate USP | Penetration enhancer | 8% w/v |
| Povidone USP | Thickener | 1-5% |
| Purified water USP | Vehicle | 10% v/v |
| Isopropyl alcohol USP | Vehicle | 30% v/v |
| Alcohol USP | Vehicle | To 100% v/v |

Various alterations, modifications and/or additions may be introduced into the constructions and arrangement of parts previously described without departing from the spirit or ambit of the invention. More specifically the features of any one of the embodiments may be added to other embodiments resulting in an implement that combines features of more than one embodiment.

We claim:

1. A method of increasing the testosterone blood level of a person in need thereof comprising applying to at least one axilla of the person a liquid pharmaceutical composition comprising testosterone and a carrier wherein said composition is applied with an implement comprising:
a support; and
a receptacle mounted on the support and defining a reservoir space with an open top and being configured to receive the liquid in the reservoir space through the open top, wherein the receptacle includes a flexible membrane integrally forming a base and a wall, the wall being substantially transverse to the base and having a working surface configured to spread the liquid over the treatment surface, wherein the base has a continuous surface such that liquid cannot pass through the base, wherein the wall includes an inner portion which extends from the base to an upper end and an outer skirt portion, wherein the inner portion and skirt portion form a double-wall structure, and wherein at least the wall is resiliently deformable so in use the working surface maintains contact with the treatment surface when spreading the liquid.

2. A method according to claim 1, wherein the liquid pharmaceutical composition comprises:
   (a) a pharmaceutically effective amount of testosterone;
   (b) one or more of lower alkyl alcohols; wherein the combined amount of lower alkyl alcohols is at least 60% v/v of the composition;
   (c) one or more penetration enhancers; and
   (d) a viscosity modulating agent for increasing the viscosity of the composition.

3. A method according to clam 2, wherein the one or more penetration enhancers is selected from the group consisting of fatty acids, fatty acid esters, fatty alcohols, glycols and glycol esters, 1,3-dioxolanes and 1,3-dioxanes, macrocyclic ketones containing at least 12 carbon atoms, oxazolidinones and oxazolidinone derivatives, alkyl-2-(N,N-disubstituted amino)-alkanoate esters, (N,N-disubstituted amino)-alkanol alkanoates, sunscreen esters and mixtures thereof.

4. A method according to claim 2, wherein the one or more penetration enhancers is selected from the group consisting of glycols, oleic acid, isopropyl myristate, cyclopentadecanone, sorbitan monooleate, octisalate, octyldimethyl-para-aminobenzoate, octyl para-methoxycinnamate, and combinations thereof.

5. A method according to claim 1 wherein the liquid is in the form of a lotion or gel.

6. A method according to claim 1 wherein the liquid has a viscosity greater than water and less than 300 centipoise.

7. A method according to claim 1 wherein the person is a male suffering hypogonadism and the liquid is applied to provide a serum testosterone level in the range of from 300 to 1000 ng/dl.

8. A method according to claim 1 wherein the liquid pharmaceutical composition comprises the penetration enhancer in an amount of from 0.01% to 15% w/v of the liquid.

9. A method according to claim 1 wherein the support of the implement is detachably connectable to a container containing the liquid and which is provided with a pump dispenser for delivering the liquid from the container and the method comprises delivering the volume of liquid from the container to the receptacle for application to the treatment surface.

10. A method according to claim 9 wherein the support is detachably connected to the container and surrounds the pump so as to reduce the likelihood of inadvertent discharge from the pump.

11. A method according to claim 1 wherein the support is relatively rigid in comparison to at least the wall of the receptacle so that at least the wall is movable relative to the support when applying the liquid.

12. A method according to claim 1 wherein the method further comprises applying a volume of the liquid to the reservoir space;
   and deforming the wall of the receptacle containing the volume of liquid against the treatment surface of the subject and spreading the liquid over the treatment surface comprising at least one axilla of the subject using the working surface.

13. A method of increasing the testosterone blood level of a person in need thereof comprising applying to at least one axilla of the person a liquid pharmaceutical composition comprising testosterone and a carrier wherein said composition is applied with an implement comprising:
   a support; and
   a receptacle mounted on the support and defining a reservoir space with an open top and being configures to receive liquid in the reservoir space through the open top,
   wherein the receptacle includes a flexible membrane integrally forming a base and a wall, the wall being substantially transverse to the base and having a working surface configured to spread the liquid over the treatment surface, wherein the base has a continuous surface such that liquid cannot pass through the base,
   wherein the wall includes an inner portion which extends from the base to an upper end and an outer skirt portion; wherein the inner portion and skirt portion form a double walled structure, and
   wherein at least the wall is resiliently deformable so in use the working surface maintains contact with the treatment surface when spreading the liquid; and
   wherein the liquid pharmaceutical composition comprises:
   (i) a pharmaceutically effective amount of testosterone;
   (ii) octyl salicylate penetration enhancer in an amount of from 0.01% to 15% w/v of the liquid;
   (iii) volatile solvent selected from the group consisting of ethanol, isopropanol and mixtures thereof in a total amount of from 70% to 99% v/v of the liquid; and
   (iv) a viscosity modulating agent in an amount to provide the liquid with a viscosity greater than water and less than 300 centipoise.

14. A method according to claim 13 wherein the person is male.

15. A method according to claim 14 wherein the male is suffering hypogonadism.

16. A method according to claim 15 wherein the liquid is applied to provide a serum testosterone level in the range of from 300 to 1000 ng/dl.

17. A method according to claim 13 wherein the support of the implement is detachably connectable to a container containing the liquid and which is provided with a pump dispenser for delivering the liquid from the container and the method comprises delivering the volume of liquid from the container to the receptacle for application to the treatment surface.

18. A method according to claim 13 wherein the support is detachably connected to the container and surrounds the pump so as to reduce the likelihood of inadvertent discharge of the liquid from the pump.

19. A method according to claim 13 wherein the viscosity modulating agent is polyvinyl pyrrolidone.

20. A method according to claim 19 wherein the polyvinyl pyrrolidone is present in the liquid in an amount in the range of from 1% to 3% w/v.

21. A composition according to claim 13 wherein the testosterone is present in the liquid in an amount of at least 1% w/v.

22. A composition according to claim 13 wherein the volatile solvent is present in the liquid in an amount of at least 80% v/v.

23. A method according to claim 13 wherein the method further comprises applying a volume of the liquid to the reservoir space; and deforming the wall of the receptacle containing the volume of liquid against the treatment surface of the subject and spreading the liquid over the treatment surface comprising at least one axilla of the subject using the working surface.

* * * * *

UNITED STATES PATENT AND TRADEMARK OFFICE
CERTIFICATE OF CORRECTION

PATENT NO. : 8,419,307 B2
APPLICATION NO. : 13/464556
DATED : April 16, 2013
INVENTOR(S) : Peter Bayly et al.

It is certified that error appears in the above-identified patent and that said Letters Patent is hereby corrected as shown below:

In the Claims:

Column 16, Claim 21, line 62, please delete "A composition according to claim 13" and insert -- A method according to claim 13 --.

Column 16, Claim 22, line 65, please delete "A composition according to claim 13" and insert -- A method according to claim 13 --.

Signed and Sealed this
Second Day of July, 2013

Teresa Stanek Rea
*Acting Director of the United States Patent and Trademark Office*